(12) United States Patent
Klemperer (10) Patent No.: US 8,757,158 B2
(45) Date of Patent: *Jun. 24, 2014

(54) MOUTHPIECE, NASAL SEAL, HEAD APPLIANCE, APPARATUS, AND METHODS OF TREATING SLEEP APNEA

(76) Inventor: Walter G. Klemperer, Champaign, IL (US)

(*) Notice: Subject to any disclaimer, the term of this patent is extended or adjusted under 35 U.S.C. 154(b) by 983 days.

This patent is subject to a terminal disclaimer.

(21) Appl. No.: 11/213,648

(22) Filed: Aug. 29, 2005

(65) Prior Publication Data

US 2005/0279367 A1    Dec. 22, 2005

Related U.S. Application Data

(62) Division of application No. 10/106,838, filed on Mar. 26, 2002, now Pat. No. 7,000,611.

(51) Int. Cl.
*A61M 16/00* (2006.01)

(52) U.S. Cl.
USPC ............. 128/206.29; 128/204.18; 128/207.11

(58) Field of Classification Search
USPC ............. 128/204.18, 205.25, 206.29, 207.11, 128/206.27, DIG. 26, 206.12, 206.13, 128/206.21, 206.28, 202.27
See application file for complete search history.

(56) References Cited

U.S. PATENT DOCUMENTS

| | | | | |
|---|---|---|---|---|
| 3,139,088 A | * | 6/1964 | Galleher, Jr. | 128/206.29 |
| 3,692,025 A | * | 9/1972 | Greenberg | 128/857 |
| 4,090,518 A | * | 5/1978 | Elam | 128/207.15 |
| 4,098,270 A | * | 7/1978 | Dolby | 128/206.12 |
| 4,200,114 A | * | 4/1980 | Waite | 131/178 |
| 5,361,416 A | * | 11/1994 | Petrie et al. | 2/171.2 |
| 5,431,158 A | * | 7/1995 | Tirotta | 128/206.21 |
| 5,638,814 A | * | 6/1997 | Byrd | 128/207.17 |
| 5,687,715 A | * | 11/1997 | Landis et al. | 128/207.18 |
| D410,089 S | * | 5/1999 | Schiavoni | D24/191 |
| 5,996,581 A | * | 12/1999 | Duch | 128/206.26 |
| 6,526,978 B2 | * | 3/2003 | Dominguez | 128/207.14 |
| 6,615,834 B2 | | 9/2003 | Gradon et al. | |
| 6,679,257 B1 | | 1/2004 | Robertson et al. | |
| 6,701,926 B2 | * | 3/2004 | Olsen et al. | 128/207.11 |
| 6,789,541 B2 | | 9/2004 | Olsen et al. | |
| 6,915,801 B2 | * | 7/2005 | Pokras | 128/201.27 |
| 6,951,218 B2 | | 10/2005 | Gradon et al. | |
| 6,997,186 B2 | | 2/2006 | Robertson et al. | |
| 7,152,602 B2 | | 12/2006 | Bateman et al. | |

FOREIGN PATENT DOCUMENTS

WO    WO 01/95965    6/2001

OTHER PUBLICATIONS

Hart, "The OPAP Dental Applicance," printed from web, dated Nov. 11, 1999.
Hart, FDA Document dated Oct. 18, 1999, Re: K991926.
OPAP Health Care, picture of OPAP.
Talk about sleep archives, "New Oral Interface May Appeal to Sleep Apnea Patients," May 29, 2001.

* cited by examiner

*Primary Examiner* — Patricia Bianco
*Assistant Examiner* — Camtu Nguyen
(74) *Attorney, Agent, or Firm* — Frank Rosenberg (57) ABSTRACT

A CPAP device and a method for treating sleep apnea use a head appliance with an oral adaptor comprising a tube partially inserted in a person's mouth and a diaphragm applied over the tube against the mouth, such that the lips are formed into a tight seal with the tube. A nasal seal is described comprising two rollers to which a strap is attached, so that the nasal seal is easily put in place, adjusted and maintained by rolling the rollers on the nose sides or pulling the straps.

17 Claims, 12 Drawing Sheets

TO HUMIDIFIER

MOUTHPIECE, NASAL SEAL, HEAD APPLIANCE, APPARATUS, AND METHODS OF TREATING SLEEP APNEA

RELATED APPLICATION

This application is a divisional of U.S. patent application Ser. No. 10/106,838, filed Mar. 26, 2002, now U.S. Pat. No. 7,006,611.

BACKGROUND

Sleep apnea is a common sleep ailment that affects as many as five percent of the population worldwide. Persons with sleep apnea stop breathing for short durations many times during sleep, so that the depth and quality of their sleep is reduced. As a result, persons with sleep apnea suffer from a profound sleepiness, which can impair their ability and performance at work and in other activities.

Sleep apnea often results from a collapse of the person's throat tissues during sleep, which reduces or suppresses the air flow to the lungs. Lowered oxygen levels and increased carbon dioxide levels in blood alert the person's brain and breathing resumes, but each occurrence arouses the person and interrupts restorative sleep.

Surgery is a possible treatment but surgical procedures are complex and success rates are often low. A more common treatment for sleep apnea is to force air inside the person's throat during sleep with a respirator apparatus. Apparatuses of this type use continuous positive airway pressure or CPAP.

Respirator apparatuses traditionally provide pressurized air or gas to a nasal mask which is applied to the persons' nose during sleep. However, nasal masks are difficult to apply on a person's nose, which results in skin irritation, nasal congestion, airways dryness, and air leaks. In addition, nasal masks are bulky, so that the person wearing the mask cannot move easily and may experience claustrophobia.

SUMMARY OF THE INVENTION

In view of the above, there is a need for an apparatus allowing a person having sleep apnea to breathe regularly without interruption during sleep, which is easy and comfortable to wear, does not leak unintentionally, and effectively maintains the open state of the airways.

The present invention provides such an apparatus. In particular, the present invention provides an oral adaptor or mouthpiece that allows a respirator to apply positive pressure in a person's airways without leaks and without irritation or congestion, and a nasal seal or seal that is easy and comfortable to wear and effectively avoids unintentional leaks. The present invention also provides a head appliance that includes such a mouthpiece and a nasal seal, as well as an apparatus and method for treating sleep apnea or symptoms of sleep apnea.

In an aspect of the present invention, an oral adaptor for a CPAP (Continuous Positive Airway Pressure) device comprises: an oral insert having a passage therein, comprising an insertion portion to be inserted into a person's mouth and a connection portion for connecting the oral insert to a CPAP respirator, and a sealing element to be placed on the person's mouth, wherein the sealing element is a flexible material such that the person's lips form a seal on the oral insert. In some embodiments, the sealing element can be a diaphragm or a pad.

In another aspect of the present invention, an oral adaptor to be applied to a person's mouth comprises: a tubular portion having an insertion end to be inserted in a person's mouth and a connection end to be connected to a source of positive pressure, and a first surface which faces an inner side of a person's lips, and a second surface which faces an outer side of the person's lips, when the oral adaptor is applied to the person's mouth, such that the person's lips are conformed between the second surface and at least one of the tubular portion and the first surface when a positive pressure is created inside the mouth to form a seal with the oral adaptor.

In another aspect of the present invention, a nasal seal for a CPAP device comprises two curved pieces to be placed on respective sides of a person's nose, which are connected to each other so as to leave a space between the curved pieces for the person's nose, wherein a holding strap is attached to the nasal seal for application on the person's nose. In one embodiment, the curved pieces are rollers rotatable around respective axes, the axes being connected to each other so as to leave a space between the rollers for the person's nose.

In another aspect of the present invention, a head appliance comprises an oral adaptor or a mouthpiece as described above, a nasal seal as described above, or both.

In another aspect of the present invention, a head appliance for a CPAP device comprises: a mouthpiece having an insertion portion to be inserted in a person's mouth and a connection portion to be connected to a CPAP respirator, a connection tube having an end connected to the connection portion of the mouthpiece, a head strap to be placed over a persons' head, and a tube support element attached to the head strap for supporting the connection tube.

In yet another aspect of the present invention, a CPAP device comprises a head appliance as described above connected to a CPAP respirator.

In a further aspect of the present invention, a method for treating symptoms of sleep apnea in a person comprises: inserting an insertion portion of an oral insert in the person's mouth, applying a sealing element on the person's mouth so that the person's lips form a tight seal around the insertion portion of the oral insert, and connecting the oral insert to a source of positive pressure.

In another aspect of the present invention, a method for treating symptoms of sleep apnea in a person comprises: inserting an insertion portion of an oral insert in the person's mouth such that a first surface of the insertion portion faces an inner side of the person's lips, applying a sealing element on the person's mouth such that a second surface faces an outer side of the person's lips, so that the lips form a tight seal around the insertion portion of the oral insert, and connecting the oral insert to a source of positive pressure.

In various embodiments, advantages of the present invention may include: the smaller overall size of the head gear, which facilitates movements of the sleeper, the absence of nasal CPAP, which reduces airways irritation and congestion, the reduction or elimination of unintentional leaks, which avoids airways dryness and improves efficiency, the ease of application of the head gear and the softness of the contact between the elements of the head gear and the skin, which makes wearing the head gear more comfortable. The nasal seal is able to be removed easily. In particular, the present invention can make it possible to essentially eliminate unintentional leaks.

DESCRIPTION OF PARTICULAR EMBODIMENTS

Figure 1:
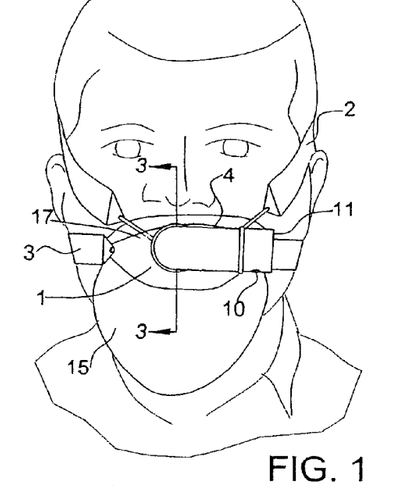
FIG. 1 is a front view of a first embodiment of a head appliance according to the present invention mounted on a person's head.
Figure 2:
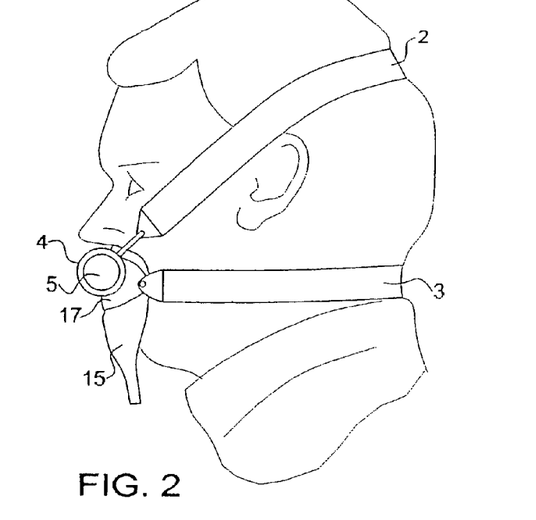
FIG. 2 is a side view of the head appliance of FIG. 1.
Figures 3A, 3B, 3C:
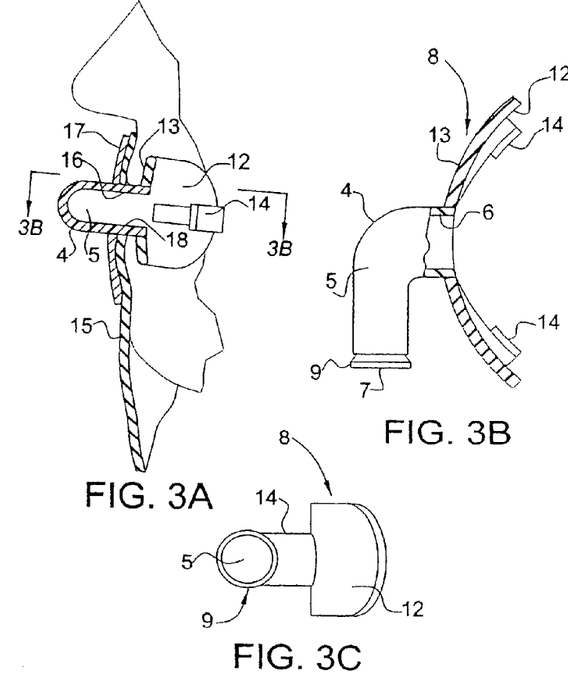
FIG. 3A is a vertical cross-sectional view of the head appliance of FIG. 1 along line 3-3 of FIG. 1.
FIG. 3B is a horizontal cross-sectional view of an oral adaptor of the head appliance along line B-B of FIG. 3A.
FIG. 3C is a perspective view of the oral adaptor of FIG. 3B.
Figure 3D:
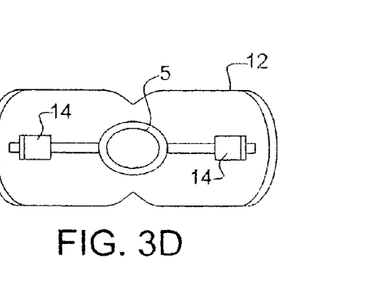
FIG. 3D is a view of the oral adaptor of FIG. 3B along arrow D on FIG. 3B.
Figure 3E:
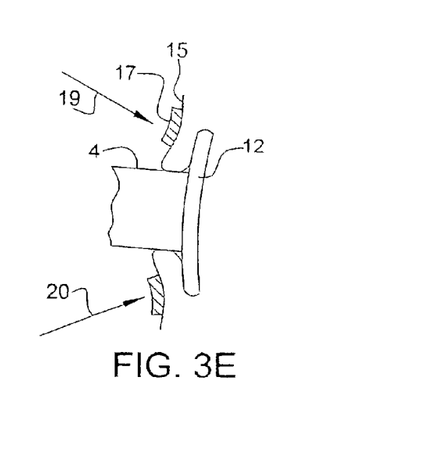
FIG. 3E is a schematic partial vertical cross-sectional view of the head appliance of FIG. 1 along line 3-3 of FIG. 1 without a diaphragm to show lip positions.

FIGS. 1-3 show a first embodiment of a head appliance for a CPAP device according to the present invention, which is mounted on a person's head. The head appliance comprises an oral adaptor 1, which is applied as a mouthpiece to the mouth of the person. The oral adaptor 1 is partially inserted into the person's mouth and is maintained against the person's mouth by a first strap 2 and a second strap 3 passed around the person's head.

The oral adaptor comprises a tube 4, which defines a passage 5 for air or gas having an opening 6 inside the mouth and an opening 7 outside the mouth. The tube has the general shape of an L. One branch of the L forms an insertion portion 8 that is inserted into the person's mouth. The other branch of the L defines a connection portion 9 for connecting the oral adaptor to an air or gas supply hose of an apparatus for applying a positive pressure to the airways by means of pressurized air or gas. Also, an exhaust port is located on the tube or between the tube and the apparatus for applying a positive pressure. In this embodiment, the oral adaptor is connected to the supply hose by a snapped connection, which makes it easy to connect and disconnect the oral adaptor to the supply hose. The insertion portion 8 carries a peripheral flange 12, which is positioned between the teeth (not shown) and the inner sides of the person's lips. Thus, the inner sides of the lips face a surface 13 of the peripheral flange that is oriented toward the corner of the L shape. The peripheral flange 12 has substantially a butterfly shape in this embodiment and the insertion portion 8 of the tube has an oval shape in the area where it meets the peripheral flange. Further, the flange 12 is advantageously dimensioned so as to fill the space between the lips and the teeth and gums around the mouth, and the outer edge of the flange is tapered, rounded, or both tapered and rounded, so as to protect the adjacent mouth tissues and to improve the sealing effect of the inner lips against the flange.

At least one biting bit 14 is located at the inner end of the insertion portion to aid positioning of the oral adaptor in the mouth. For example, two biting bits, each having a mushroom shape, are attached at the inner surface of the peripheral flange 12 on the sides of the air or gas passage as shown on FIG. 3. An oral insert comprising a tube with a flange and biting bits is sold for example as part of a snorkel under the mark AIR DRY by the TECHNISUB company. Advantageously, the biting bit heads have rectangular shapes and extend to the outer periphery of the flange on each side, and the biting bit leg has dimples that allow the teeth to grip it.

In a variant (not shown), the exhaust port is located on a tube section branched on the tube of the oral adaptor, for example in the area of the L corner. In that case, the oral adaptor can have substantially a T shape. One branch of the T defines the insertion portion and a second branch of the T defines a connection portion for connecting the oral adaptor to the apparatus for applying a positive pressure, as in the tube having a L shape. However, in this variant, the exhaust port is located on the third branch of the T. This variant reduces the amount of expelled carbon dioxide that returns to the mouth upon inhalation.

On the outer side of the lips is applied a sealing element in the form of a diaphragm 15. The diaphragm 15 is large enough so as to completely cover the mouth and the lips from the outside. In this embodiment, the diaphragm 15 extends beyond the outer limit of the lips. The diaphragm is made of flexible material so that its shape conforms itself to the shape of the outer side of the lips when the diaphragm is applied to the lips. The diaphragm has a hole 16 for passing it over the tube. Preferably, the hole 16 has a shape and dimension equal to or less than those of a cross-section of the tube 4 at the location of the lips, so that a tight fit is provided between the diaphragm 15 and the tube 4 when the diaphragm is applied to the lips. The diaphragm is separate from the tube. In the alternative, the diaphragm could be integral with (such as by molding) or attached to the tube, for example by a glue, tape or staple connection, although care should be taken to avoid configurations that unduly irritate the skin.

Advantageously, the diaphragm 15 is less rigid than the peripheral flange 12 on the insertion portion 8 of the tube 4. Thus, the inner side of the lips is applied against the surface of the peripheral flange 12 when the insertion portion is positioned inside the mouth, and the outer side of the lips is firmly maintained without excessive pressure by the diaphragm 15 covering the mouth. As a result, the lips form a tight seal without leak against the tube 4, or at least between the peripheral flange 12 and the diaphragm 15. An even tighter seal is obtained by application of petroleum jelly or like substance in the space between the peripheral flange and the diaphragm where the lips surround the tube 4, on the tube itself, and/or on the lips, or by the secretion of saliva in these locations.

Preferably, the diaphragm is elastic, so that the diaphragm can stretch and/or contract to an appropriate degree before, during and/or after positioning of the diaphragm on the lips in order to obtain a tighter seal with the lips, or with the skin around the lips. For example, the diaphragm can be positioned over the lips and pulled by its sides to extend the elastic material, and then allowed to contract. For the present purposes, elastic materials are defined as materials that, when stretched 10% (more preferably 50%), for one hour, in a direction, at room temperature, experience less than 5% permanent deformation after the stress is removed. In a preferred embodiment, the elastic material comprises latex. It has been discovered that an elastic diaphragm results in a superior seal as compared to an inelastic diaphragm. Preferred materials for the diaphragm are non-porous, elastic materials that do not irritate the skin, for example natural rubber latex sold as under the mark THERABAND.

The first strap 2 maintains the tube in its position applied to the mouth. The first strap is attached to the tube 4 and passes around the person's head above the ears. Advantageously, the first strap 2 is attached to the tube 4 at a location as close as possible to the mouth, in particular, closer to the insertion portion than to an end of the oral insert opposed to the insertion portion, so that the insertion portion 8 is pulled by the strap toward the upper teeth while avoiding a lever effect which would pull the insertion portion 8 away from the bottom teeth. Also, the biting bit or bits 14 are maintained in contact with the upper teeth. At least one end of the first strap is attached to the tube 4 on the branch of the L shape which carries the insertion portion 8, i.e., closer to the insertion portion 8 than to the opposite end of the tube. The other end of the first strap 2 can be attached to the same location, or to the other branch of the L shape, which carries the connection portion 9, as shown on FIG. 1. Thus, the first strap constitutes a tube holding strap.

The second strap 3 passes around the person's head under the ears and maintains the diaphragm 15 against the outer side of the lips. The second strap 3 is not attached to the diaphragm 15, but comprises an enlarged portion 17 with a hole 18, which is passed over the tube 4 and applied against the diaphragm 15 to maintain the diaphragm against the lips. Thus, the second strap constitutes a diaphragm strap. The enlarged portion 17 of the second strap is advantageously flexible or elastic so as to conform itself to the shape of the diaphragm, i.e., to the shape of the outer side of the lips. However, the enlarged portion 17 can be of a less flexible or less elastic material than the diaphragm, provided the enlarged portion is flexible enough to maintain the diaphragm against the lips so as to avoid leaks. In an alternative embodiment, the second strap could be attached to the diaphragm, for example, by taping the diaphragm to the strap.

The enlarged portion of the second strap applies the diaphragm against the lips with a weak force that is intended to be sufficient to compensate forces tending to pull the insertion portion away from the mouth without compressing the mouth to a level which would damage the lips, gums or teeth, or other parts of the mouth. More specifically, the second strap applies forces 19 and 20 that are directed so as to push the lips toward the flange 12 and toward the tube 4, with the force component directed toward the tube (vertical component on FIG. 3E) is comparable to the force component directed toward the flange (horizontal component on FIG. 3E). In the case of an elastic diaphragm, the forces are preferably sufficient to maintain the diaphragm in an appropriately extended state, so as to obtain a tight seal with the lips or with the skin around the lips.

In a variant of this embodiment, the diaphragm could be integral with or attached permanently or removably to the second strap. However, in the present embodiment, the diaphragm extends above and below the enlarged portion of the second strap to facilitate positioning and application over the lips without folds or creases, and, in the case of an elastic diaphragm, to facilitate pulling the sides of the diaphragm in order to obtain a tighter seal.

Each strap has a ribbon shape and is adjustable in length, for example, by elasticity or with Velcro® (hooks and loops), with a buckle, with an elastic portion, with buttons, or combinations of these. It is noted that several variants are possible for the straps other than the ones described above. Thus, in alternative embodiments, each or both of the first strap and second strap are attached to a part of the oral adaptor or are separate from the oral adaptor, only one strap or more than two straps are provided, or the oral adaptor is held between the person's lips without any strap. Each of the straps may be elastic or comprise an elastic portion, or it may have a length that does not vary between adjustments. Suitable materials for the straps or portions of the straps include, but are not limited to, fabric, flexible material, for example plastic, and an elastic material such as rubber.

Figure 4:
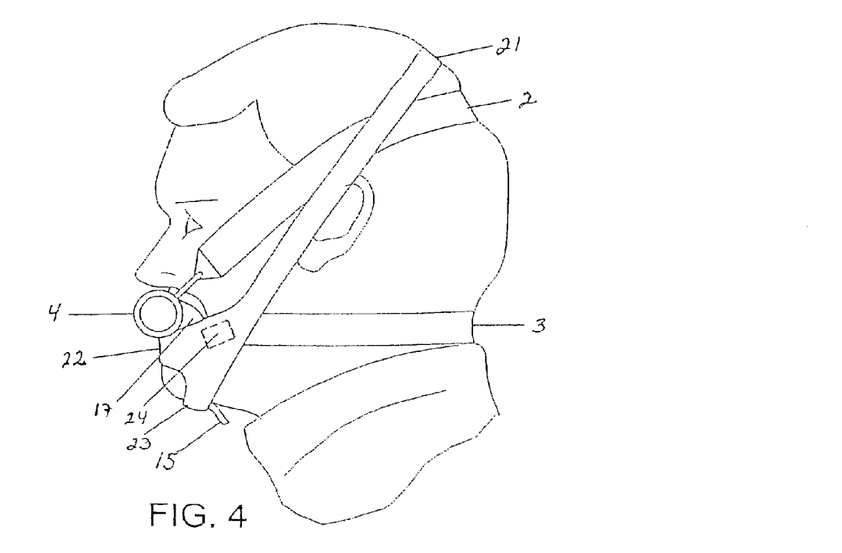
FIG. 4 is a side view of a second embodiment of a head appliance according to the present invention, further comprising a jaw strap mounted on the person's head.

FIG. 4 shows a second embodiment of a head appliance according to the present invention, which is identical to the head appliance of FIGS. 1-3 except that a jaw strap 21 is provided around the person's head over the first and second straps. The jaw strap 21 has a ribbon shape and passes above the ears and over the chin. In the area of the chin, the jaw strap is divided in two segments 22 and 23, one above a central part of the chin, the other under a central part of the chin, so that the central part of the chin is not covered by the jaw strap.

An advantage of the jaw strap 21 is that it prevents the lower jaw from dropping excessively, as occurs for some persons when they sleep, which could create leaks. The jaw strap can also help in maintaining the diaphragm by pressing its lower portion against the person's skin under the mouth. Additionally, the jaw strap passes over the cheeks, so as to prevent ballooning of the cheeks, which could loosen the lips from around the tube. Thus, the jaw strap complements the other straps, in particular the second strap, which may prevent ballooning of tissue around the lips. In the alternative, the jaw strap could be provided to fulfill only some of these objectives.

In addition, at least one pressure element or portion 24 (shown in dotted line on FIG. 4) is located on the person's face over the cheeks beyond the location facing the extremities of the peripheral flange, for example at opposite ends of the diaphragm or under one of the straps. In a preferred embodiment, there is a larger peripheral flange so that the sealing elements do not extend beyond the location facing the extremities of the flange. The pressure portions 24 are pressed by the strap or straps against the cheeks and tend to push the cheeks inward, which improves the seal formed by the lips between the peripheral flange 12 and the diaphragm 15 and between the tube 4 and the diaphragm 15. The pressure portions 24 may be unattached or attached to another part of the device, for example the diaphragm or one of the straps, for example the diaphragm strap 3 or the jaw strap 17.

Figure 5:
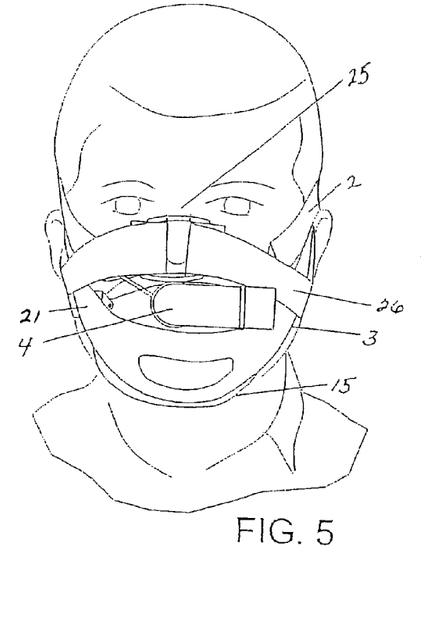
FIG. 5 is a front view of a third embodiment of a head appliance according to the present invention, further comprising a nasal seal mounted on the person's head.
Figure 6:
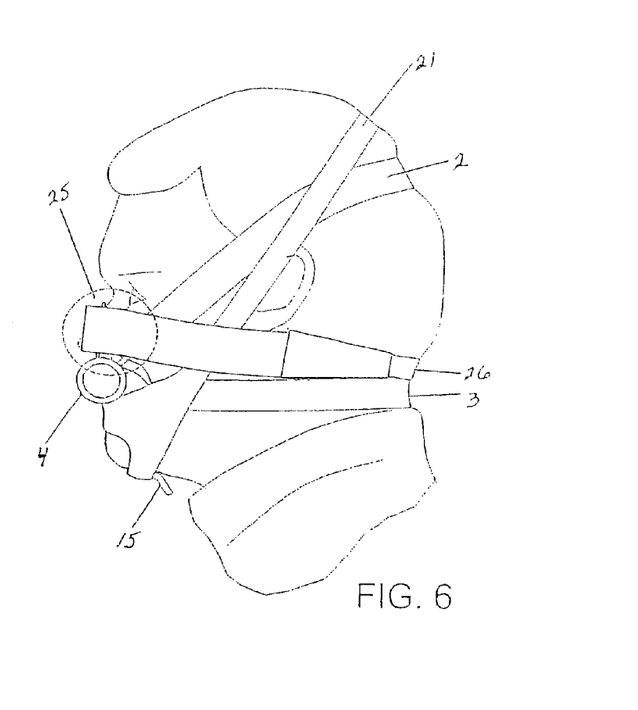
FIG. 6 is a side view of the head appliance of FIG. 5.

FIGS. 5-6 show a third embodiment of a head appliance according to the present invention, which is identical to the head appliance of FIG. 4 except that a nasal seal 25 is provided on the person's nose. The nasal seal is applied to both sides of the nose to close the nostrils and is maintained by a nasal seal strap 26 that passes around the person's head.

Figure 9A:
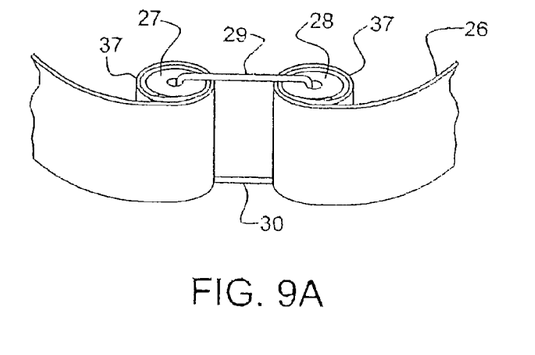
FIG. 9A is a partial perspective view of the nasal seal of FIG. 7.
Figure 9B:
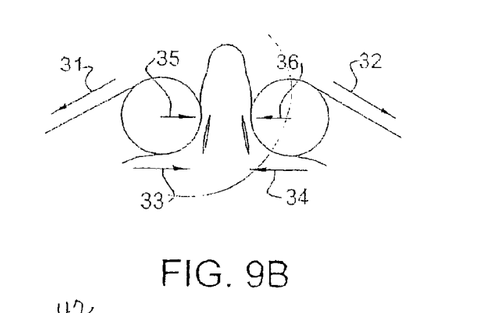
FIG. 9B is a schematic partial horizontal cross-sectional view of the head appliance of FIG. 7 along line 9-9 on FIG. 8 showing the positioning of the nasal seal on the nose.

An embodiment of a nasal seal is shown in more detail in FIG. 9. It comprises two curved pieces 27 and 28 disposed at a distance from each other. In the embodiment described in the figures, the curved pieces are rollers rotatable around axes, which are connected at their ends by at least one connection member, preferably elastic members 29 and 30, so that an adjustable space for the nose is defined between the rollers. In a variant, each of the cylinders has an aperture therethrough, and the elastic connection comprises an elastic band that moves through the aperture in each cylinder. The rollers are preferably made or comprise at least a layer or a portion of a flexible material, for example an elastic material. Advantageously, the ends of the nasal strap are connected to the rollers such that the rollers are rotated in opposite direction when the nasal strap is pulled, as shown by the upper arrows 31 and 32 on FIG. 9B.

The rollers close the nostrils primarily by applying shear forces to the skin next to the base of the nose, which tends to pull the skin next to the nose on both sides of the nose toward the base of the nose, as shown by the lower arrows 33 and 34 on FIG. 9B. In other words, the rollers are located in the corners formed by the nose faces and the skin adjacent to the nose base without directly pressing on the nose itself. Thus, a perfect seal can be obtained without any compressive force on the nose itself, which protects the fragile skin of the nose from being damaged when the nasal seal is applied for long periods of time, for example, a full night. In a variant, the rollers secondarily apply a slight compressive force to a region of the nose closer to the tip as shown by the middle arrows 35 and 36 on FIG. 9B, so as to close the nostrils in that region. In another variant, the rollers are located against the nose faces and apply a compressive force appropriate to close the nostrils so as to obtain an airtight seal. In that case, the nasal seal can be applied against the nose faces without touching the base of the nose. Any remaining opening can be filled with petroleum jelly so as to obtain a perfect seal.

The nasal strap 26 helps obtain or maintain a good positioning of the rollers 27 and 28 against the nose because if the rollers are moved away from the person's face, the strap pulls the rollers, which tends to make them roll toward the face. As a result, a tight seal is obtained without applying a strong force on the nose or around the head. For example, as shown on FIG. 9A, the strap ends are connected to and rolled around the peripheral surface of the rollers. The nasal strap can have features similar to the other straps described above. The strap ends are preferably a soft material 37 that does not irritate the skin.

The proper balance between forces, i.e., to obtain high shear force and low compressive force, is obtained by adjusting one of several of (a) the circumference of the rollers, (b) the cleanliness of the face (no greasiness), (c) the nature of the roller surface (high coefficient of friction), (d) the size and elastic properties of the elastic members, (e) the elastic properties of the holding strap, and (f) the amount of tension of the holding strap.

Figure 7:
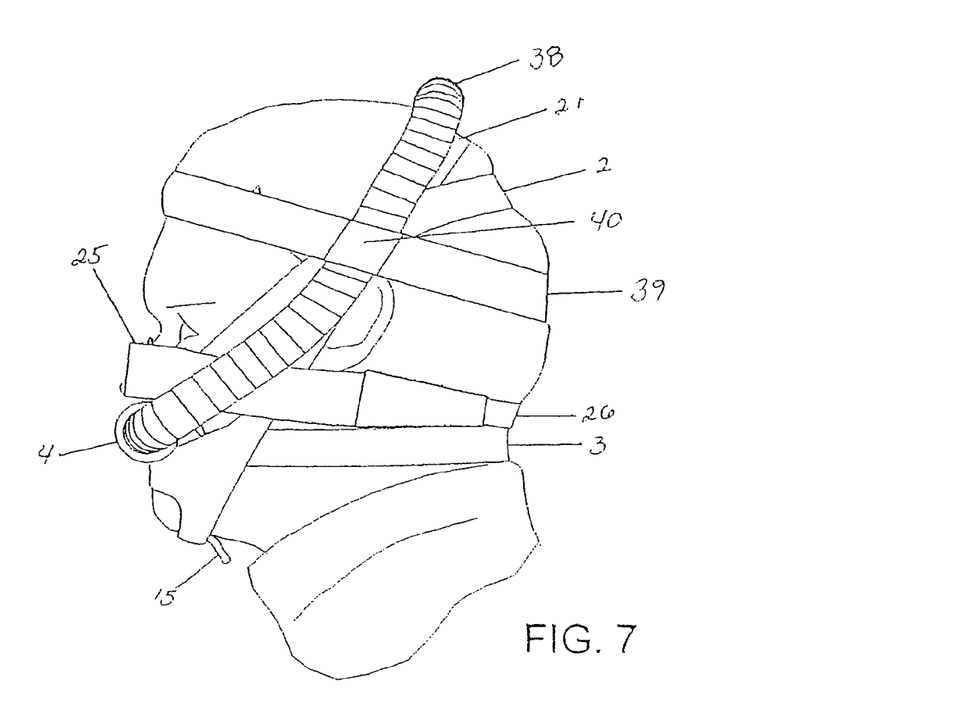
FIG. 7 is a side view of a fourth embodiment of a head appliance according to the present invention, further comprising a head strap and a connection tube.
Figure 8:
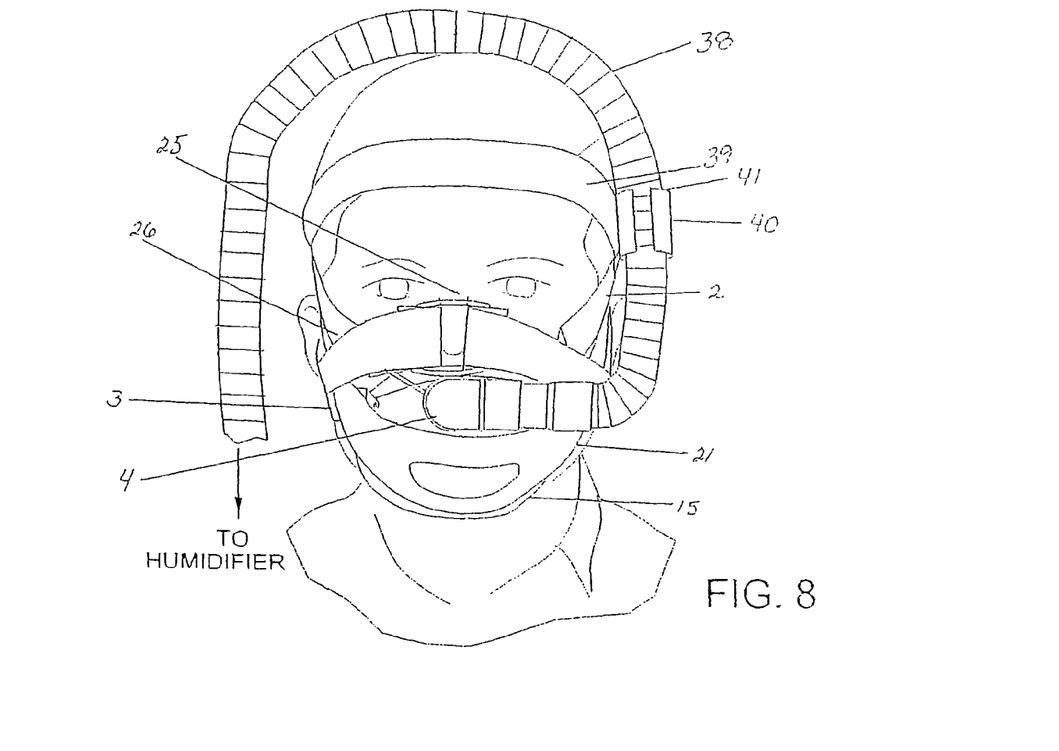
FIG. 8 is a front view of the head appliance of FIG. 7.

FIGS. 7 and 8 show a fourth embodiment of a head appliance according to the present invention, which is identical to the head appliance of FIGS. 5-6 except that it additionally comprises a connection hose 38 connected to the tube 4 of the oral adaptor 1 for connecting the head appliance to the source of positive air or gas pressure or to a respirator. The connection hose 38 is preferably made of a flexible or elastic material and able to change shape, so that movements of the person's head are not prevented, but is sufficiently rigid to maintain a passage for air or gas from the respirator, in particular when it is submitted to radial or torsional forces. Advantageously, the oral adaptor can freely rotate with respect to the connection hose.

A head band 39 passes around the person's head above the ears and the face. A hose support 40 is attached to the head band on the same side of the head as the connection portion of the oral adaptor. The hose support is in the shape of an open or closed ring that defines a passage 41 for the connection hose. The connection hose can slide and rotate inside the ring. However, in the case of an open ring, the diameter of the connection hose is larger than the width of the cut portion of the ring, so that the connection hose cannot be removed through the cut portion of the ring, except by collapsing the hose or by widening the cut portion of the ring when the ring is not completely rigid. The head band is, for example, a conventional elastic head band, and the hose support is, for example, a snorkel hose support from a snorkel sold under the mark AIR DRY by the TECHNISUB company.

The exhalation port is mounted on the connection portion of the oral adaptor between the tube and the connection hose. For example, the exhalation port is located on a connection section which is freely rotatable with respect to at least one of the oral adaptor and the connection hose for the CPAP respirator. In a variant not shown, the exhalation port could be located on a branched passage opening in the passage between the insertion portion and the connection portion. The exhalation port allows expired air to exit the passage but prevents air from the outside to penetrate into the passage. A suitable exhalation port (for example, 10, 11 in FIG. 1) is sold for example under the mark WHISPER SWIVEL by the RESPIRONICS company.

Figure 10:
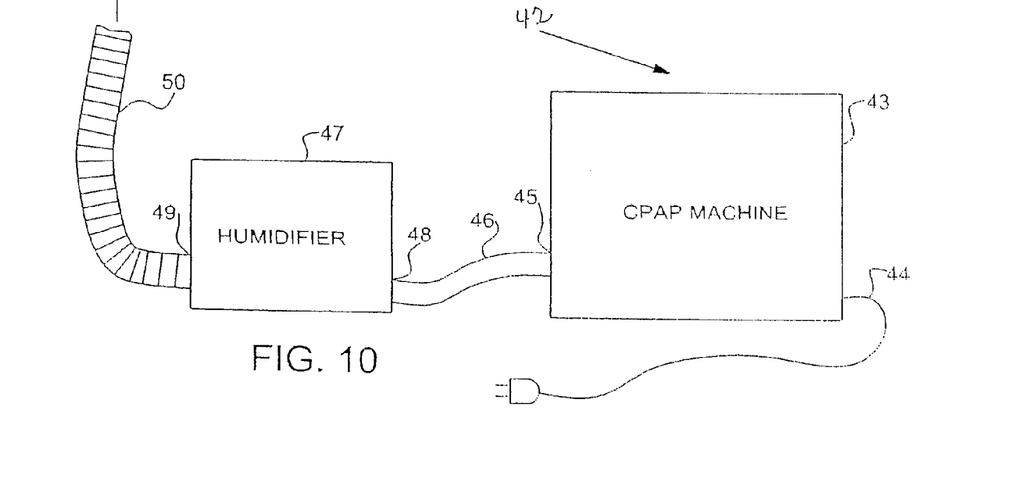
FIG. 10 is a schematic view of a CPAP apparatus connected to the head appliance of FIG. 7.
Figure 11:
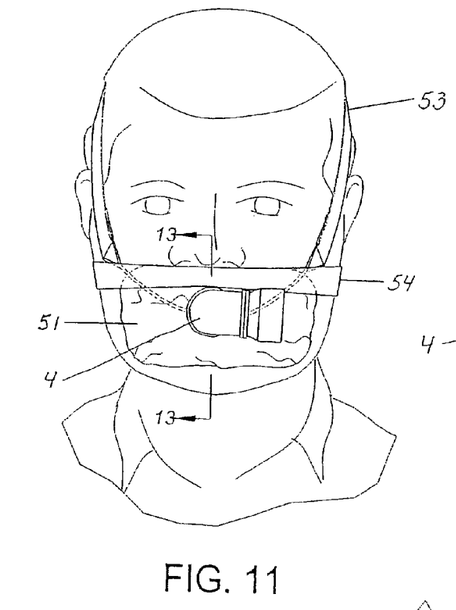
FIG. 11 is a front view of a fifth embodiment of a head appliance according to the present invention without a lower diaphragm support strap.
Figure 12:
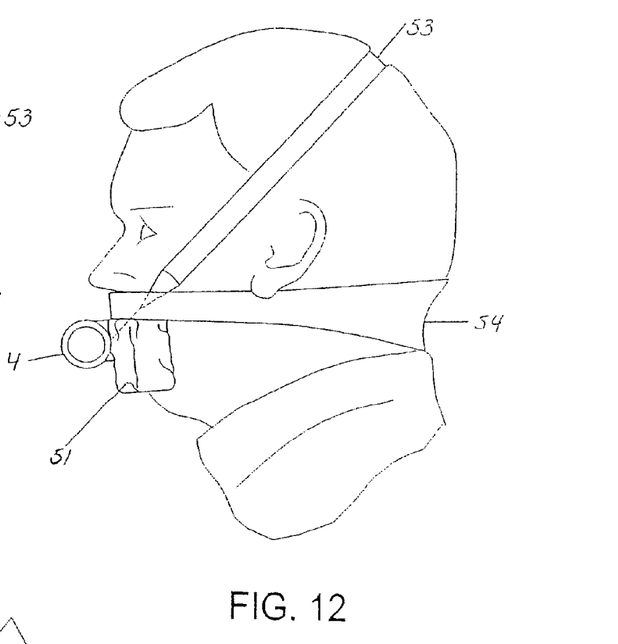
FIG. 12 is a side view of the head appliance of FIG. 11.

FIG. 10 shows schematically an embodiment of a respirator 42 that is connected to a head appliance according to the present invention to provide a source of positive pressure. The respirator comprises a CPAP device 43 that creates positive pressure. The respirator is operated with electric power through an electric wire 44 which may be plugged to a power outlet (not shown). The respirator provides a positive pressure to an outlet 45. A suitable respirator is for example the CPAP machine sold under the RESPIRONICS mark.

An end of a first hose 46 is connected to the outlet of the CPAP. Thus, positive air or gas pressure is created inside the first hose. A humidifier 47 has an inlet 48 connected to the other end of the first hose and an outlet 49 connected to an end of a second hose 50. Thus, air or gas having positive pressure and adjusted humidity content is present in the second hose. The second hose supplies air or gas to the connection hose of the head appliance or directly to the exhalation port, or the second hose constitute the connection hose. Given the absence of unintentional leaks, the humidifier can be omitted unless the person desires additional humidification of the inhaled air or gas.

The head appliance according to the above embodiments is advantageously positioned on the person's head as follows.

As a preliminary step, the person can apply petroleum jelly or the like in the nostrils and lip balm on the inner part of the outer lips. The person then prepares the insertion portion by passing the diaphragm over the tube, through the diaphragm hole, in the case of an unattached diaphragm.

Next, as a first positioning step, the person inserts the insertion portion of the oral adaptor into her mouth with the peripheral flange between the teeth and the lips, and places her lips around the tube.

Second, the person extends the diaphragm over the lips without folds or creases, and passes the tube holding strap around the head above the ears to retain the insertion portion against the upper teeth.

Third, the person passes the diaphragm strap over the tube and adjusts it around the head under the ears and over the diaphragm above and under the tube to maintain the diaphragm over the lips while forming the lips against the flange and the tube of the oral adaptor. In the case of an elastic diaphragm, the person advantageously pulls the sides or the corners of the diaphragm so as to extend it over the lips to obtain a tighter seal.

Fourth, the person places pressure elements in appropriate locations, if desired, then passes the jaw strap over the chin, the cheeks, and around the head above the ears, if a jaw strap is provided.

Fifth, the person puts on the nasal seal, if provided, by placing the rollers against the facial skin adjacent to the nose, against the skin of the nose faces, or both, and by rotating the rollers toward the face and/or pulling the strap to rotate the rollers. As a result, the rollers roll on the skin toward the nose base and are pulled toward each other by the elastic members until the nostrils are totally collapsed. By adjusting the tension of the strap before or after positioning the rollers, an adequate shear force can be applied by the rollers against the facial skin or the nose sides to maintain a secure seal without excessive compressive force against the nose.

Sixth, the person connects the oral adaptor to the air or gas supply hose of the respirator. When positive pressure is applied inside the mouth, the lips are further molded and wedged against the tube between the peripheral flange and the diaphragm. As a result, a secure seal can be obtained in the area of the mouth also. In the case of an elastic diaphragm, a better seal may be obtained if the diaphragm, a better seal can be obtained if the diaphragm is again adjusted, as discussed above in the third step. If provided, the connection hose is connected between the oral adaptor and the air or gas supply hose and positioned in the hose support of the head band, which is placed around the head.

FIGS. 11-15 show a fifth embodiment of a head appliance according to the present invention. In this embodiment also, the head appliance comprises an oral adaptor. The oral adaptor comprises a tube and a diaphragm that are substantially similar to the tube and diaphragm of the first to fourth embodiments. However, this fifth embodiment is different from the first to fourth embodiments in particular in that a pad 51 that is dimensioned so as to cover the person's lips is applied over the diaphragm. The pad is made of a relatively thick layer of flexible and resilient or elastic material, for example a rubber foam. The inner face 52 of the pad can cover the diaphragm partially or completely as shown on FIG. 13.

As in previous embodiments, the diaphragm can be unattached, integral, or attached permanently or removably to the tube. Further, the head appliance comprises straps for supporting the tube and maintaining the diaphragm. The tube holding strap 53 is substantially identical to the first strap in the first to fourth embodiments. However, the other straps may be different from the other straps in the first to fourth embodiments. For example, the single diaphragm strap is replaced by an upper diaphragm strap 54 and a lower diaphragm strap 55. The lower diaphragm strap is shown on FIGS. 14-15 but not on FIGS. 11-13.

Figure 14:
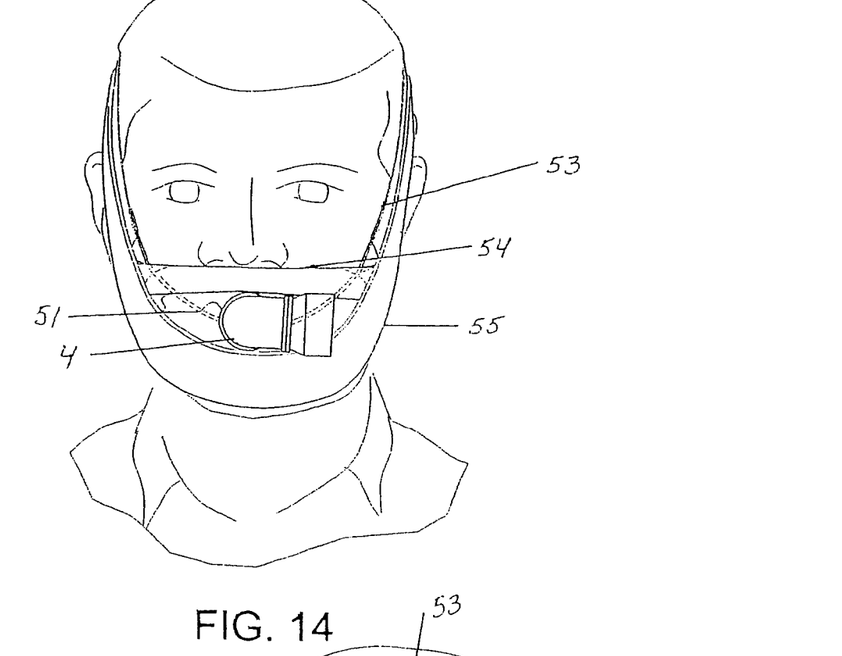
FIG. 14 is a front view of the head appliance of FIG. 11 with the lower diaphragm support strap.
Figure 15:
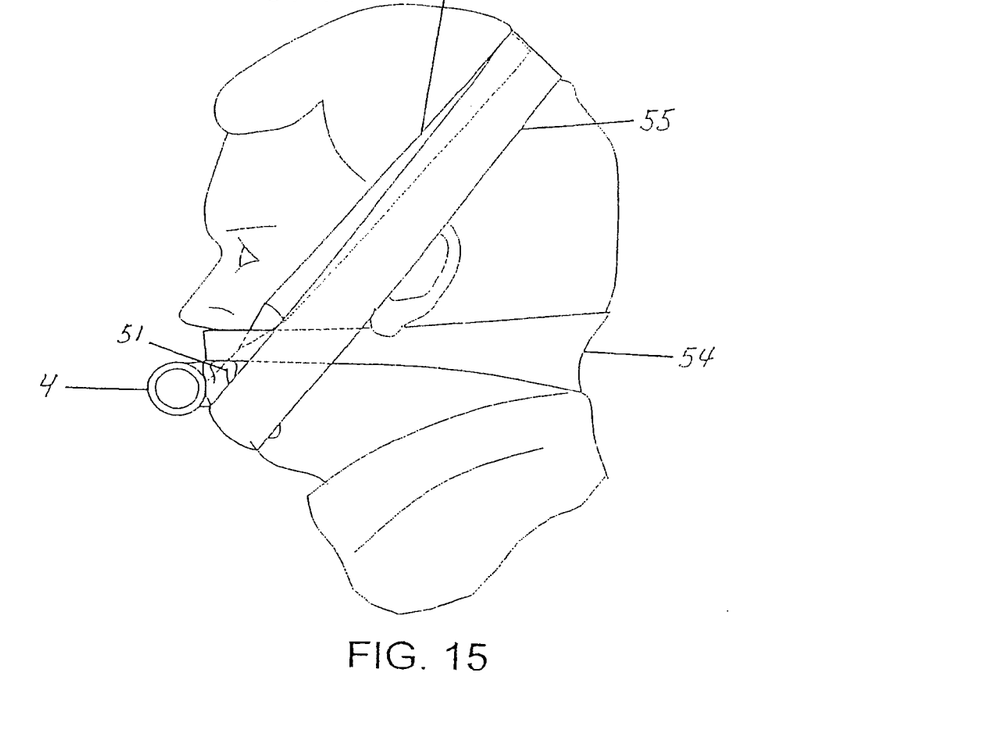
FIG. 15 is a side view of the head appliance of FIG. 11 with the lower diaphragm support strap.

The upper diaphragm strap 54 is in the form of a band that surrounds the head under the ears and is applied on an upper portion of the sealing pad 51 above the tube, i.e., over and above the upper lip but under the nose. The lower diaphragm strap 55 is in the form of a band that surrounds the head above the ears and is applied on a lower portion of the sealing element 51 under the tube, i.e., over and under the lower lip, and above or over at least a portion of the chin. Thus, the upper diaphragm strap 54 maintains the upper portion of the diaphragm against the upper lip and the lower diaphragm strap 55 maintains the lower portion of the diaphragm against the lower lip. The lower diaphragm strap 55 can also function as a jaw strap to maintain the mouth closed during sleep, avoid ballooning of the cheeks, and apply pressure portions (not shown) on the lip edges or on the cheeks.

A suitable upper diaphragm strap is sold for example as SNUG FIT model "chin strap" by MALLINCKRODT company, and a suitable lower diaphragm strap is sold as CHIN STRAP model under the mark RESPIRONICS.

Figure 13:
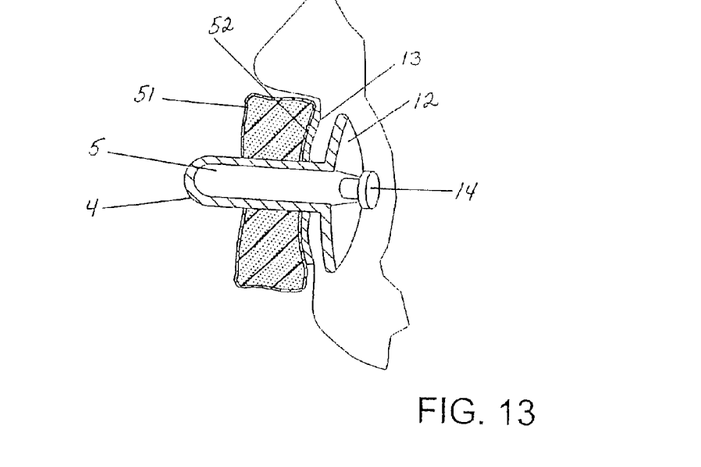
FIG. 13 is a cross-section al view of the head appliance of FIG. 11 along line 13-13 of FIG. 11.

In this embodiment, the pad participates in distributing, equalizing, or both, the forces exerted by the upper and lower diaphragm support straps to the diaphragm, so as to improve the seal between the diaphragm and the lips or the skin around the lips, while protecting the skin against excessive localized pressure. Thus, the inner face 52 of the pad may be contoured so as to have a shape corresponding to the shape of a person's lips, for example with a central recess which can be positioned over the lips.

Figure 16:
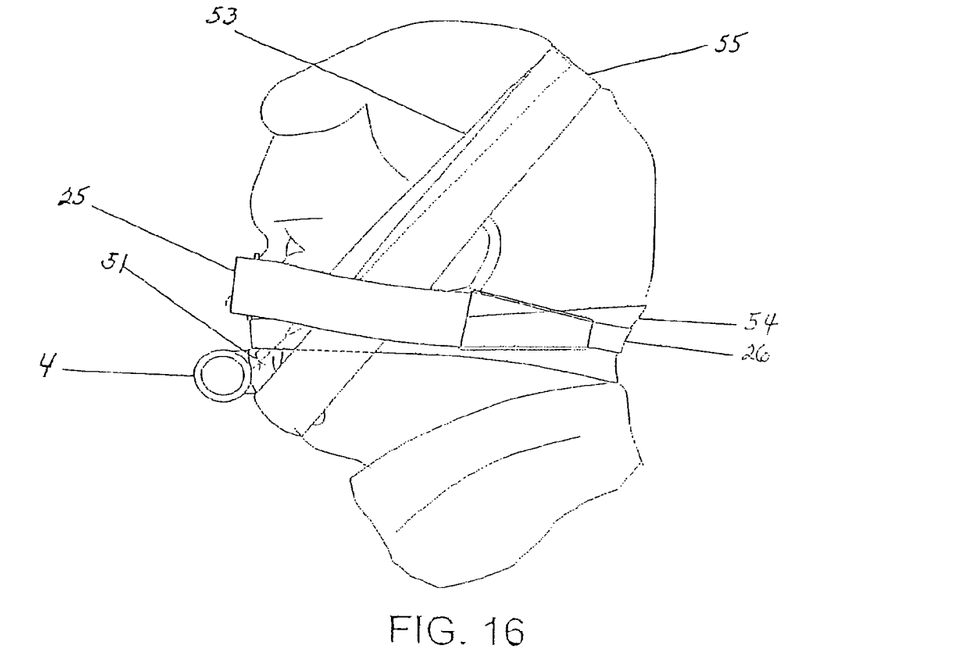
FIG. 16 is a side view of a sixth embodiment of a head appliance according to the present invention, further comprising a nasal seal.
Figure 17:
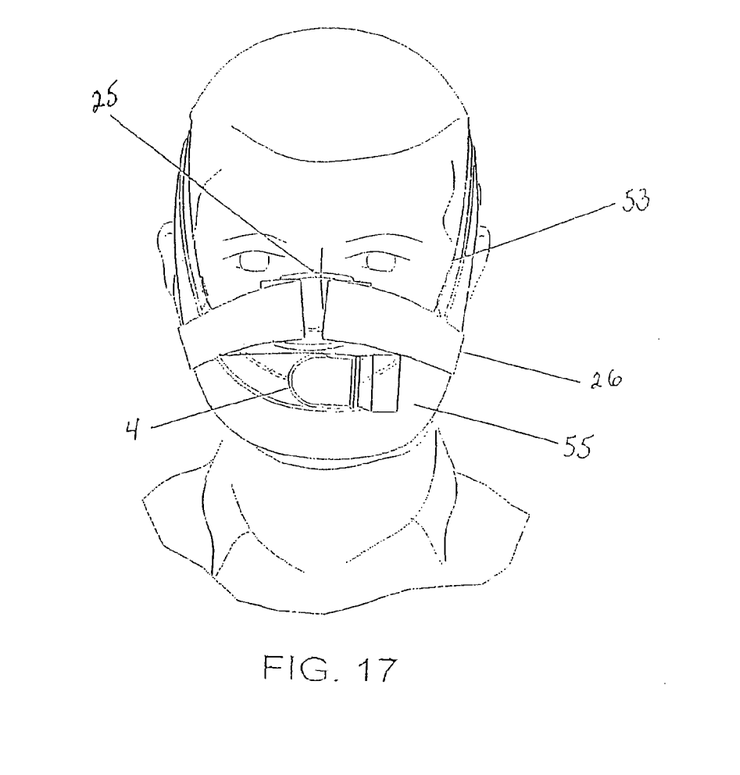
FIG. 17 is a front view of the head appliance of FIG. 16.

FIGS. 16-17 show a sixth embodiment of the head appliance according to the present invention. In this sixth embodiment, the head appliance is identical to the head appliance of the fifth embodiment except that it additionally comprises a nasal seal. The nasal seal is identical to the nasal seal in the third and fourth embodiments.

Figure 18:
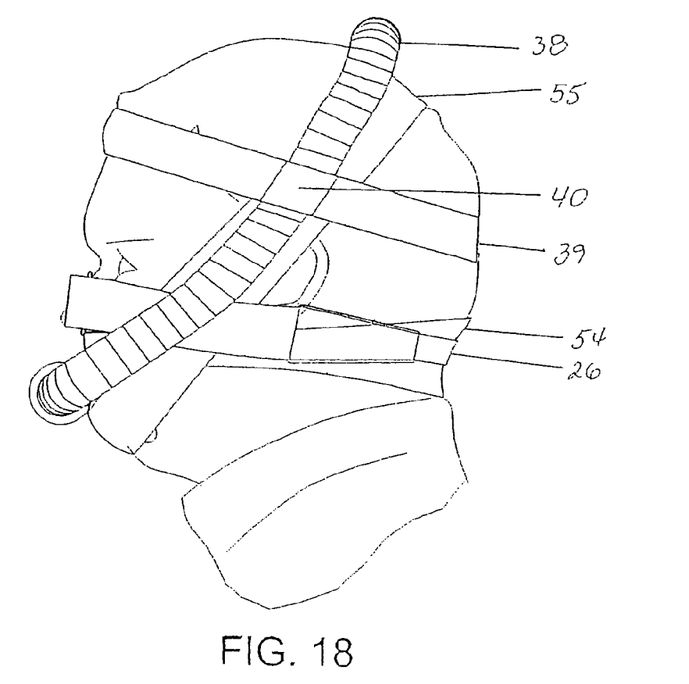
FIG. 18 is a side view of a seventh embodiment of a head appliance according to the present invention, further comprising a nasal seal.
Figure 19:
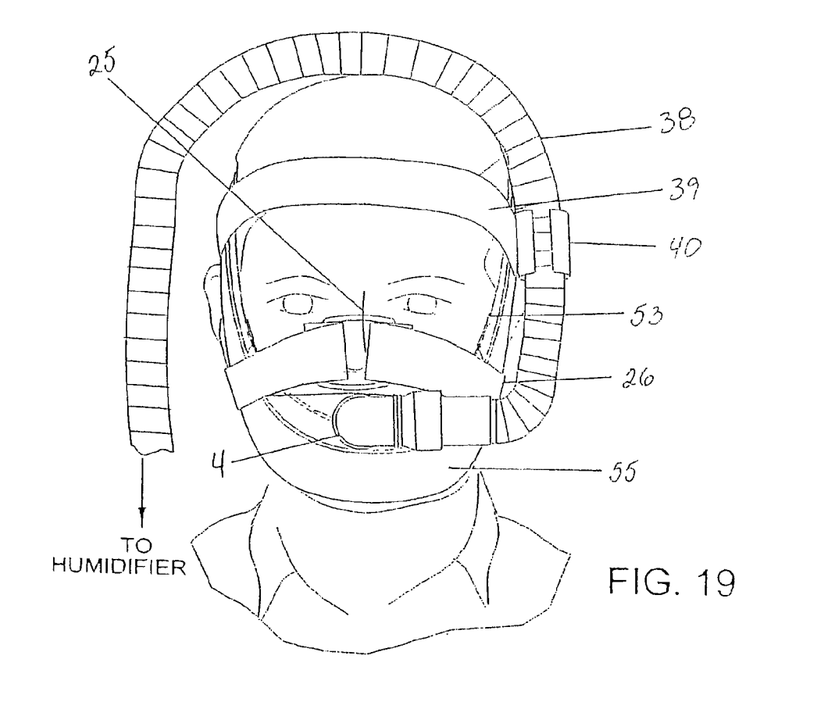
FIG. 19 is a front view of the head appliance of FIG. 18.
Figure 20:
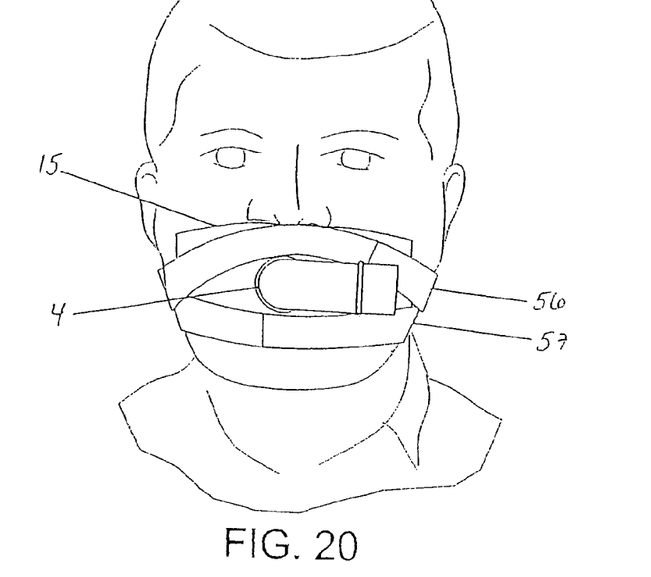
FIG. 20 is a front view of an eighth embodiment of a head appliance according to the present invention, further comprising a connecting hose support.
Figure 21:
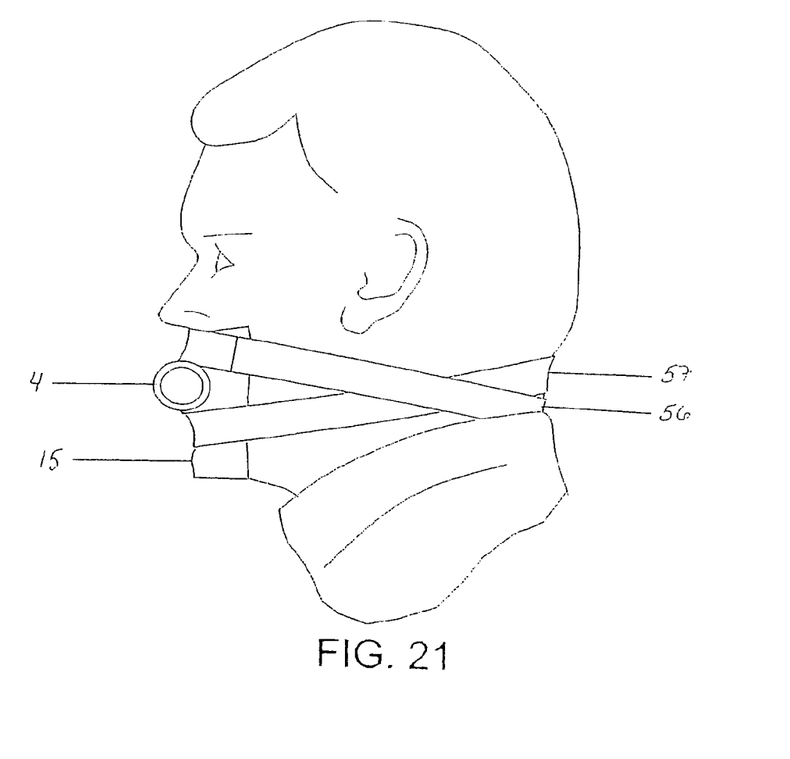
FIG. 21 is a side view of the head appliance of FIG. 20.
Figure 22:
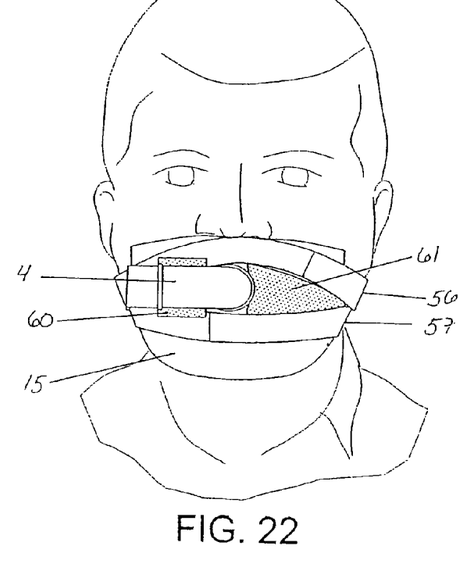
FIG. 22 is a front view of a ninth embodiment of a head appliance according to the present invention, further comprising pressure elements and a jaw strap, shown without a jaw strap.
Figure 23:
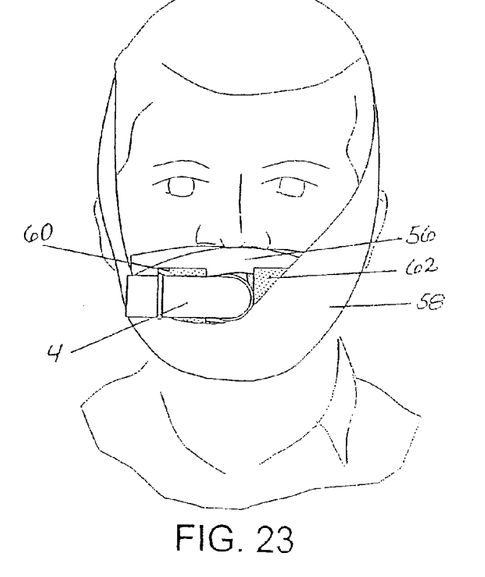
FIG. 23 is a front view of the head appliance of FIG. 22, shown with the jaw strap.
Figure 24:
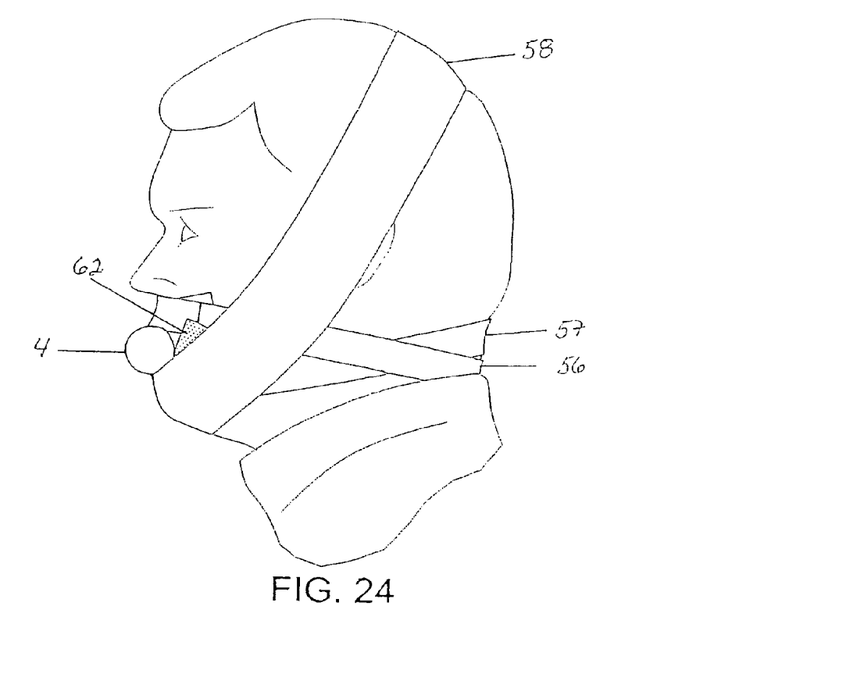
FIG. 24 is a side view of the head appliance of FIG. 23.
Figure 25:
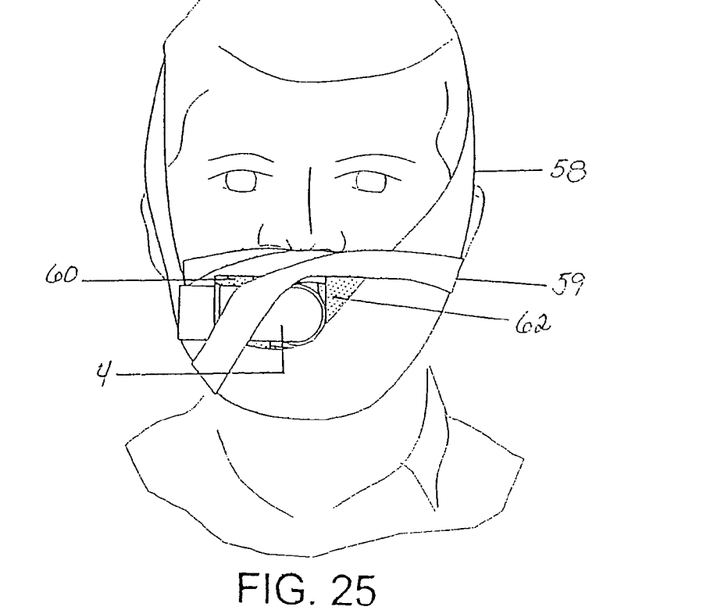
FIG. 25 is a front view of a tenth embodiment of a head appliance according to the present invention, further comprising a tube holding strap.
Figure 26:
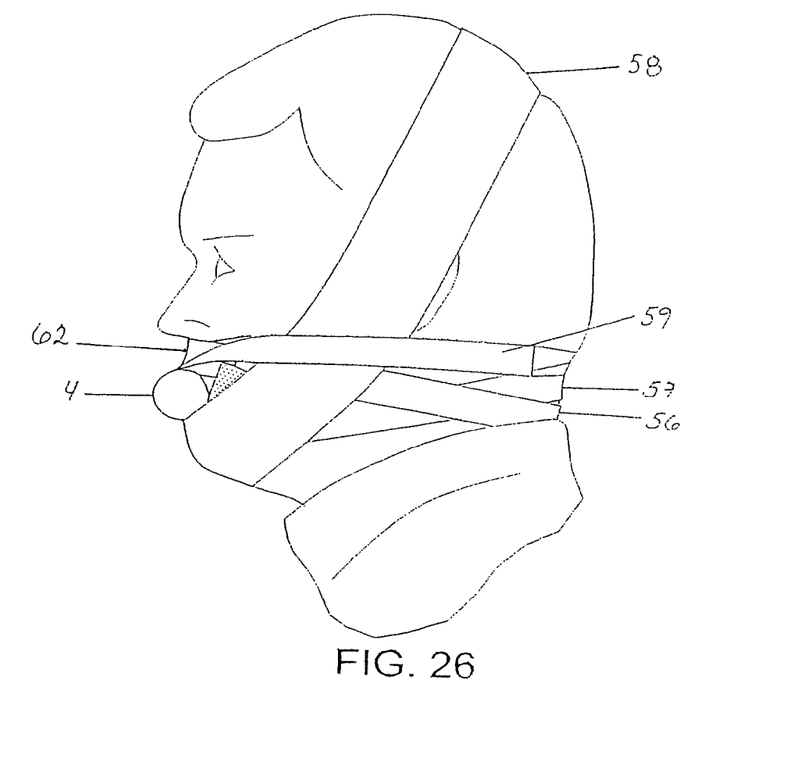
FIG. 26 is a side view of the head appliance of FIG. 25.
Figure 27:
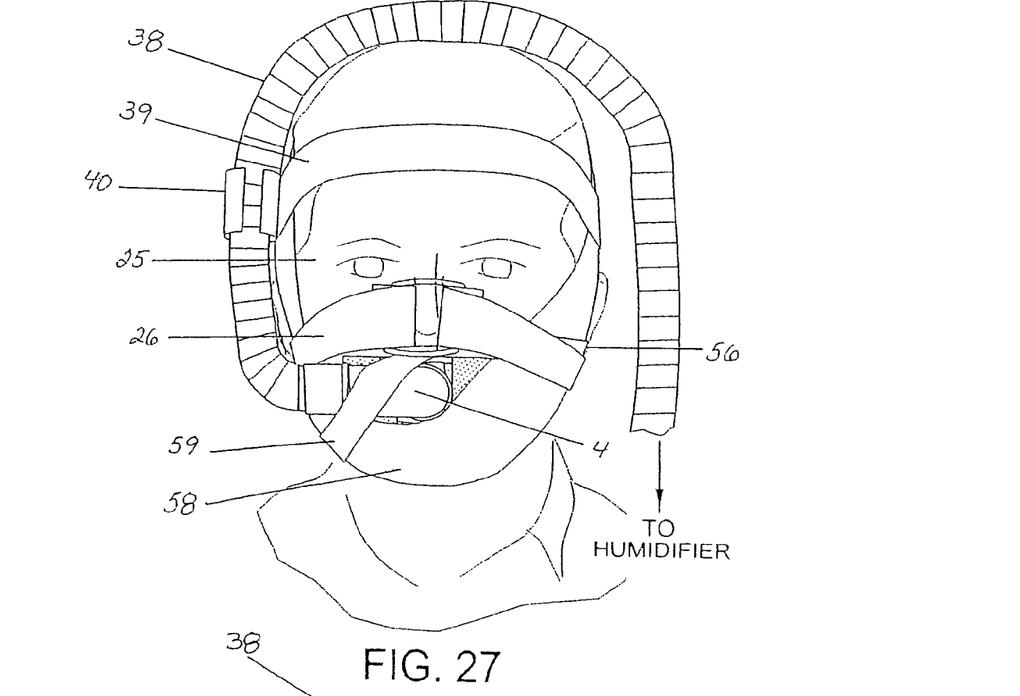
FIG. 27 is a front view of an eleventh embodiment of a head appliance according to the present invention, further comprising a nasal seal and a connecting hose support.
Figure 28:
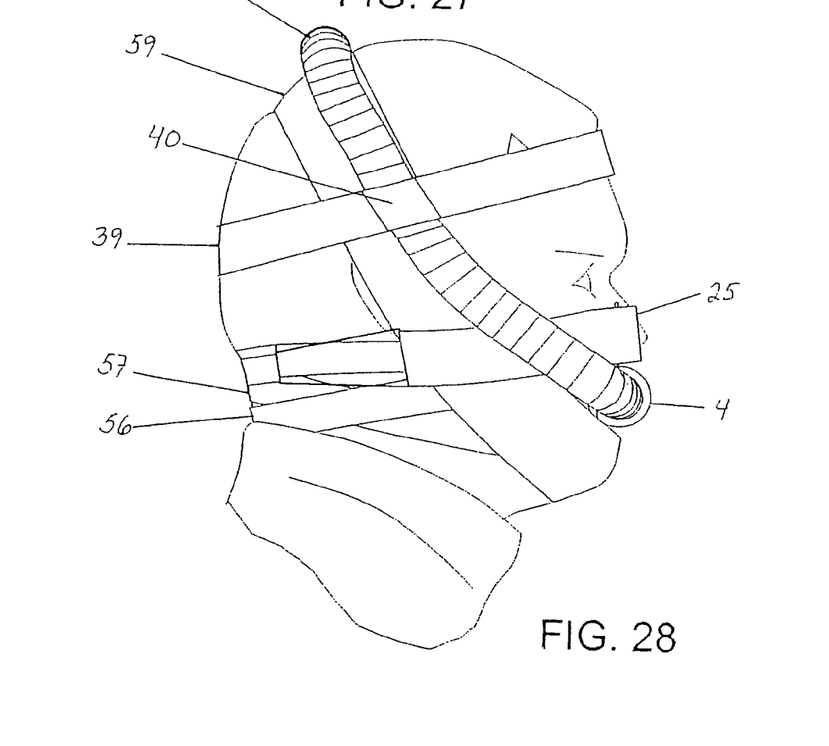
FIG. 28 is a side view of the head appliance of FIG. 27.

FIGS. 18-19 show a seventh embodiment of the head appliance according to the present invention, in which the head appliance is identical to the head appliance of the sixth embodiment except that it additionally comprises a connection hose with head band and hose support, which are substantially identical to those of the fourth embodiment.

In variants of the embodiments of FIGS. 11-19, as in other embodiments of the present invention, the diaphragm extends advantageously below and under the maintaining elements such as straps or pads, so as to allow adjustment of the diaphragm to avoid leaks. The diaphragm is advantageously rectangular or oval in shape with dimensions adapted to extend beyond the mouth on each side.

The head appliance according to the fifth to seventh embodiments of the present invention is positioned on the person's head as follows.

First, the person places the insertion portion of the oral insert into her mouth with the peripheral flange between the teeth and the lips, and places the lips around the tube. This operation is facilitated when the person bites into the biting bits.

Second, the person fully extends the diaphragm over the mouth, then passes the tube holding strap around the head above the ears to pull the insertion portion against the upper teeth.

Third, the person positions the pad over the diaphragm, then places the upper diaphragm strap, for example by passing the strap around her head below the ears, and fastens it over the upper portion of the pad under her nose.

Fourth, the person places the lower diaphragm strap, for example by passing over the lower part of the pad and over the ears, then fastening it at the top of her head. As a result, the straps cooperate to keep the pad in place, so that the diaphragm is maintained against the lips but is prevented from separation from the respective lips by the pad and the straps. The actual force applied by the straps can be very low, i.e., just sufficient to maintain the pad, and additional pressure portions if provided, in place against the face.

Fifth and sixth, the person then puts on the nasal seal and the head band, if provided, and connects the connection hose or the supply hose to the oral adaptor. Once a positive pressure is created within the airways, the nasal seal can be readjusted, and the lips moved against the diaphragm to obtain a perfect seal around the tube with zero leaks. Advantageously, the lips are expanded and moved outward to contact the diaphragm, so that only lip tissue, not skin tissue, contact the diaphragm.

FIGS. 20-28 show additional embodiments of head appliances according to the present invention, which is substantially similar to the first to fourth embodiments except that the diaphragm is maintained over the lips by respective upper and lower diaphragm straps 56 and passing around the back of the person's neck, under the ears, and over the diaphragm above and under, respectively, the tube of the oral adaptor. Further, a jaw strap 58 and a tube holding strap 59, which are shown respectively on FIGS. 23-26 and 27-28, are additionally provided around the person's head. Additional pressure portions are provided over the sides of the lips or adjacent skin tissues, i.e., a first pressure portion 60 under the connection portion of the tube and a second pressure portion 61 between the upper and lower diaphragm straps on the side of the oral adaptor opposed to the connection portion. Further, in this embodiment, a third pressure portion 62 is applied on the second pressure portion 61. The jaw strap is applied over at least one of these pressure portions, here, the second and third pressure portions. The tube holding strap is applied over the connection portion 9 of the tube of the oral adaptor, i.e., over the first pressure portion.

Thus, the diaphragm is maintained over the lips by the upper and lower diaphragm straps 56 and 57, the mouth is kept closed by the jaw strap 58, and the oral adaptor is held by the tube holding strap 59, while ballooning effects and corresponding leaks are avoided by the jaw strap 58 and the pressure portions 60-62 on the mouth edges or on the cheeks.

In any of the embodiments shown in the figures, the tube of the oral adaptor has the connection portion on the left side of the person's face. It will be immediately apparent that the connection portion could also be located on the right side, or in front of the person's mouth, the connection hose passing for example around the person's nose. Also, the oral adaptor could have two connection portions on each side of the person's face, which could be connected alternatively to a connection hose and a seal, or connected simultaneously to a connection hose having a double connection end passing for example over the person's face. In the alternative, the connection portion or portions of the tube of the oral adaptor could have an elbow so as to direct its end toward the top of the person's head instead of toward its side.

The hose or hoses connecting the oral adaptor to the respirator are advantageously long enough to enable movement of the person during sleep and also to enable locating the respirator away from the person's bed. For example, the overall length of the hose or hoses may be preferably at least six feet.

Advantages of the head appliance according to the present invention include a very tight seal around the mouth without application of high pressure or strong forces which could irritate or damage the skin or be uncomfortable. Rather, a perfect seal is obtained "passively" by conforming the lips around the tube between the peripheral flange and the sealing element, with the air pressure providing the force necessary to press the lips against the sealing element. This is obtained by adjusting the forces applied by the straps so that the sealing element applies a relatively low pressure force on the lips toward the flange and a relatively high shear force on the lips toward the tube. As a result, the lips are sealed against the tube and ballooning of the lips by the formation of air pockets between the lips and the flange are effectively prevented without damaging the skin on and around the lips.

Particular embodiments of the present invention include one or more of the following: the elements in contact with the skin are soft; other than the exhalation port, no element of the head appliance is rigid—so the sleeper can roll over without a rigid component creating leverage that could create leaks; the head appliance is compact; no element extends away from the head significantly farther from the nose, which gives more freedom of movement without leverage on the mouthpiece or nasal seal, i.e., without creating unintentional leaks. Accordingly, the head appliance is very robust. Lubrication around the lips is not necessary, unless the person desires additional sealing. Lubricants, such as petroleum jelly, may be helpful to form a seal in the nose.

CLOSURE

While preferred embodiments of the present invention have been shown and described, it will be apparent to those skilled in the art that many changes and modifications may be made without departing from the invention in its broader aspects. For example, although each embodiment of the head appliance is described with one type of oral adaptor and one type of nasal seal, numerous variations are possible such as an oral adaptor of one embodiment and a nasal seal of another embodiment, and these variations are included within the scope of the invention. In particular, a person of the art will understand that one or several features of any of the described embodiment can be combined or applied to another embodiment of the present invention. The appended claims are intended to include all such changes and modifications as fall within the true spirit and scope of the invention.

The invention claimed is:

1. A head appliance for a CPAP device, comprising:
    an oral insert having a passage therein, comprising an insertion portion to be inserted into a person's mouth and a connection portion for connecting the oral insert to a CPAP respirator,
    a sealing element comprising a diaphragm to be placed on the person's mouth,
    a first strap attached to the oral insert and adapted to be passed around a person's head, and
    a second strap or jaw strap adapted to be passed around a person's head and adapted to maintain the diaphragm against the lips, or adapted to pass under the jaw to prevent the lower jaw from dropping; and wherein the insertion portion to be inserted into a person's mouth comprises a tube with an opening that is adapted to provide air inside the person's mouth.

2. The head appliance of claim 1 wherein the second strap is adapted to pass under the jaw to prevent the lower jaw from dropping.

3. The head appliance of claim 1 wherein the diaphragm is oval in shape with dimensions adapted to extend beyond the mouth on each side.

4. The head appliance of claim 1 further comprising a pad that is dimensioned so as to cover a person's lips and is adapted to be applied over the diaphragm.

5. The head appliance of claim 4 wherein the pad is made of rubber foam.

6. The head appliance of claim 1 further comprising a head band adapted to pass around a person's head above the ears and face.

7. The head appliance of claim 6 further comprising a hose support attached to the head band.

8. The head appliance of claim 1 wherein the second strap is adapted to maintain the diaphragm against the lips.

9. A head appliance for a CPAP device, comprising:
an oral insert having a passage therein, comprising an insertion portion to be inserted into a person's mouth and a connection portion for connecting the oral insert to a CPAP respirator, a sealing element to be placed on the person's mouth,
a first strap adapted to be passed around a person's head and over a person's top lip, and
a second strap adapted to be passed around a person's head and under a person's bottom lip;
wherein the insertion portion to be inserted into a person's mouth comprises a tube with an opening that is adapted to provide air inside the person's mouth; and
further comprising a jaw strap adapted to be passed around a person's head and under a person's jaw.

10. The head appliance of claim 9 wherein the sealing element comprises a diaphragm, and further wherein a pressure portion is attached to the diaphragm; and wherein the pressure portion is adapted to press against a person's cheek to press the cheek inward.

11. The head appliance of claim 10 wherein the pressure portion is disposed on the side of the oral adaptor that is opposed to the connection portion.

12. The head appliance of claim 9 wherein a pressure portion is attached to the jaw strap.

13. The head appliance of claim 9 further comprising a tube holding strap attached to the connection portion.

14. The head appliance of claim 9 further comprising a head band adapted to pass around a person's head above the ears and face.

15. The head appliance of claim 14 further comprising a hose support attached to the head band.

16. A method of treating sleep apnea, comprising:
using a head appliance comprising an oral insert having a passage therein, comprising an insertion portion to be inserted into a person's mouth and a connection portion for connecting the oral insert to a CPAP respirator, a sealing element to be placed on the person's mouth,
a first strap adapted to be passed around a person's head and over a person's top lip, and
a second strap adapted to be passed around a person's head and under a person's bottom lip, comprising:
inserting the oral insert into a person's mouth;
adjusting the sealing element over the persons mouth to form a seal;
passing the first strap around the person's head and over the person's top lip;
passing the second strap around the person's head and under the person's bottom lip; and
passing air from a CPAP device through the oral insert into the person's mouth.

17. The method claim 16 wherein the head appliance further comprises a tube holding strap adapted to attach to the connection portion, wherein the tube holding strap holds a tube that connects the CPAP device to the oral insert.

\* \* \* \* \*